US00PP25339P2

(12) United States Plant Patent
Geibel

(10) Patent No.: US PP25,339 P2
(45) Date of Patent: Mar. 10, 2015

(54) *PELARGONIUM* PLANT NAMED 'REGSAL'

(50) Latin Name: *Pelargonium grandiflorum*
Varietal Denomination: Regsal

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 56 days.

(21) Appl. No.: 13/986,774

(22) Filed: Jun. 4, 2013

(51) Int. Cl.
*A01H 5/00* (2006.01)

(52) U.S. Cl.
USPC ..... Plt./331

(58) Field of Classification Search
USPC ..... Plt./331
See application file for complete search history.

*Primary Examiner* — Anne Grunberg
(74) *Attorney, Agent, or Firm* — C. A. Whealy

(57) ABSTRACT

A new and distinct Regal Geranium plant named 'Regsal', characterized by its upright and uniformly rounded plant habit; vigorous growth habit; freely basal branching habit; early and freely flowering habit; light red, light red purple and dark red purple-colored flowers that are held above the foliar plane on strong peduncles; and no requirement for cooling treatment for flower development.

1 Drawing Sheet

Botanical designation: *Pelargonium grandiflorum.*
Cultivar denomination: 'REGSAL'.

BACKGROUND OF THE INVENTION

The present invention relates to a new and distinct cultivar of Regal Geranium plant, botanically known as *Pelargonium grandiflorum*, and hereinafter referred to by the name 'Regsal'.

The new Regal Geranium plant is a product of a planned breeding program conducted by the Inventor in Dresden, Germany. The objective of the breeding program is to develop new early flowering Regal Geranium plants that require little to no cooling treatment for flowering.

The new Regal Geranium plant originated from a cross-pollination made by the Inventor in Dresden, Germany during the summer of 2007 of two unnamed proprietary selections of *Pelargonium grandiflorum*, not patented. The new Regal Geranium plant was discovered and selected by the Inventor as a flowering plant from within the progeny of the stated cross-pollination in a controlled greenhouse environment in Dresden, Germany during the spring of 2008.

Asexual reproduction of the new Regal Geranium plant by vegetative terminal cuttings in a controlled greenhouse environment in Dresden, Germany since October, 2008 has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Regsal'. These characteristics in combination distinguish 'Regsal' as a new and distinct Regal Geranium plant:

1. Upright and uniformly rounded plant habit.
2. Vigorous growth habit.
3. Freely basal branching habit.
4. Early and freely flowering habit.
5. Light red, light red purple and dark red purple-colored flowers that are held above the foliar plane on strong peduncles.
6. No cooling treatment required for flower development.

Plants of the new Regal Geranium differ primarily from plants of the parent selections in flower coloration. In addition, plants of the new Regal Geranium are more uniform than plants of the parent selections.

Plants of the new Regal Geranium can be compared to plants of the *Pelargonium grandiflorum* 'Pacared', disclosed in U.S. Plant Pat. No. 16,777. In side-by-side comparisons conducted in Dresden, Germany, plants of the new Regal Geranium differed from plants of 'Pacared' in the following characteristics:

1. Plants of the new Regal Geranium had shorter internodes than plants of 'Pacared'.
2. Flower petals of plants of the new Regal Geranium were more undulate than flower petals of plants of 'Pacared'.
3. Plants of the new Regal Geranium and 'Pacared' differed in flower color as plants of 'Pacared' had darker-colored flowers.
4. Plants of the new Regal Geranium had shorter peduncles (umbel stems) and pedicels (flower stems) than plants of 'Pacared'.

Plants of the new Regal Geranium can be compared to plants of the *Pelargonium grandiflorum* 'Pacasal', disclosed in U.S. Plant Pat. No. 16,750. In side-by-side comparisons conducted in Dresden, Germany, plants of the new Regal Geranium differed from plants of 'Pacasal' in the following characteristics:

1. Flower petals of plants of the new Regal Geranium were more undulate than flower petals of plants of 'Pacasal'.

2. Plants of the new Regal Geranium and 'Pacasal' differed in flower color as plants of 'Pacasal' had dark pink-colored flowers.

BRIEF DESCRIPTION OF THE PHOTOGRAPH

The accompanying colored photograph illustrates the overall appearance of the new Regal Geranium plant showing the colors as true as it is reasonably possible to obtain in colored reproductions of this type. Colors in the photograph may differ slightly from the color values cited in the detailed botanical description which accurately describe the colors of the new Regal Geranium plant.

The photograph comprises a side perspective view of a typical flowering plant of 'Regsal' grown in a container.

DETAILED BOTANICAL DESCRIPTION

The aforementioned photograph and following observations, measurements and values describe plants grown in 13-cm containers during the winter and spring in a glass-covered greenhouse in Dresden, Germany and under cultural practices typical of commercial Regal Geranium production. During the production of the plants, day temperatures averaged 18° C., night temperatures averaged 16° C. and light levels ranged from 15 kilolux to 100 kilolux. To enhance the overall plant habit, plants were exposed to eight weeks of 9° C. day/night average temperatures; however, cooling is not required for flower initiation and development. Plants were six months old when the photograph was taken and five months old when the detailed description was taken. In the detailed description, color references are made to The Royal Horticultural Society Colour Chart, 1995 Edition, except where general terms of ordinary dictionary significance are used.

Botanical classification: *Pelargonium grandiflorum* 'Regsal'.

Parentage:

*Female, or seed, parent*.—Unnamed proprietary selection of *Pelargonium grandiflorum*, not patented.

*Male or pollen parent*.—Unnamed proprietary selection of *Pelargonium grandiflorum*, not patented.

Propagation:

*Type*.—By vegetative terminal cuttings.

*Time to initiate roots, summer*.—About 18 days at temperatures of 20° C.

*Time to initiate roots, winter*.—About 22 days at temperatures of 20° C.

*Time to produce a rooted young plant, summer and winter*.—About four weeks at temperatures of 20° C.

*Root description*.—Fine, fibrous; white in color.

*Rooting habit*.—Freely branching; dense.

Plant description:

*Plant and growth habit*.—Upright and uniformly rounded plant habit; inverted triangle; densely foliated; vigorous growth habit; freely basal branching habit with numerous lateral branches developing per plant.

*Plant height, to top of umbels*.—About 30 cm.

*Plant height, to top of foliar plane*.—About 25 cm.

*Plant width*.—About 35 cm.

*Lateral branches*.—Length: About 7 cm. Diameter: About 6 mm. Internode length: About 1.5 cm. Texture: Pubescent. Color: Close to 144A.

Leaf description:

*Arrangement*.—Alternate or opposite; simple.

*Length*.—About 5.5 cm.

*Width*.—About 7.5 cm.

*Shape*.—Roughly cordate.

*Apex*.—Acute.

*Base*.—Cordate, open.

*Margin*.—Bi-serrate.

*Venation pattern*.—Palmate.

*Texture, upper and lower surfaces*.—Slightly pubescent or glabrous; leathery.

*Color*.—Developing leaves, upper surface: Close to 144A. Developing leaves, lower surface: Close to 146B. Fully expanded leaves, upper surface: Close to 137A; venation, close to 137A. Fully expanded leaves, lower surface: Close to 146B; venation, close to 146D. Zonation pattern: Not observed.

*Petioles*.—Length: About 3.5 cm. Diameter: About 3 mm. Texture, upper and lower surfaces: Pubescent. Color, upper and lower surfaces: Close to 146B.

Flower description:

*Flower arrangement and flowering habit*.—Single flowers arranged in inversely conical umbels arising from apical leaf axils; umbels displayed above the foliar plane on strong peduncles; flowers face upright to mostly outwardly; freely flowering habit; about five flowers per umbel with about ten umbels developing per plant.

*Fragrance*.—None detected.

*Flowering season*.—Early flowering habit, plants begin flowering about five months after planting; plants do not require a cooling treatment for flower initiation and development; in the garden in Germany, plants flower during the spring and again during the summer.

*Flower longevity*.—Flowers last about two weeks on the plant; flowers not persistent.

*Umbel height*.—About 7.5 cm.

*Umbel diameter*.—About 9 cm.

*Flower diameter*.—About 5.5 cm.

*Flower depth (height)*.—About 3 cm.

*Flower buds*.—Length: About 1.5 cm. Diameter: About 6 mm. Shape: Spindle-shaped. Color: Close to 146B.

*Petals*.—Quantity per flower: Five or occasionally six arranged in a single whorl; two upper and three or four lower petals; petals imbricate. Length, upper petals: About 4 cm. Length, lower petals: About 3.7 cm. Width, upper petals: About 4 cm. Width, lower petals: About 2.7 cm. Shape, all petals: Obovate. Apex, all petals: Rounded. Base, all petals: Cuneate. Margin, all petals: Entire; undulate. Texture, all petals, upper and lower surfaces: Smooth, glabrous; velvety. Color, upper petals: When opening and fully opened, upper surface: Close to 58C; center, close to 59A; towards the base, close to 155D; venation, close to 59A. When opening and fully opened, lower surface: Close to 54D; center, close to 59B; towards the base, close to 155D; venation, close to 59C. Color, lower petals: When opening and fully opened, upper surface: Close to 46D; small center marking, close to 58B; towards the base, close to 155D; venation, close to 59A. When opening and fully opened, lower surface: Close to 56D; towards the base, close to 155D; venation, close to 59C.

*Sepals*.—Quantity per flower: Five to seven arranged in a single whorl. Length: About 1.8 cm. Width: About 4 mm to 7 mm. Shape: Lanceolate. Apex: Acute; somewhat reflexing. Margin: Entire. Texture, upper and lower surfaces: Pubescent. Color, upper and lower surfaces: Close to 146B.

*Peduncles* (*umbel stems*).—Length: About 6 cm. Diameter: About 3 mm. Strength: Strong; flexible. Angle: Slightly outwardly slanted. Texture: Slightly pubescent. Color: Close to 146B.

*Pedicels* (*individual flower stems*).—Length: About 3 cm. Diameter: About 2 mm. Strength: Strong; flexible. Texture: Pubescent. Color: Close to 146B.

*Reproductive organs*.—Androecium: Stamen quantity per flower: About ten. Anther length: About 2 mm. Anther shape: Tubular. Anther color: Close to 179A. Pollen amount: Abundant. Pollen color: Close to 167A. Gynoecium: Pistil quantity per flower: One. Pistil length: About 2 cm. Stigma shape: Six-parted. Stigma color: Close to 59A. Style length: About 1.5 cm. Style color: Close to 59C. Ovary color: Close to 147C. Seeds and fruits: Seed and fruit development have not been observed on plants of the new Regal Geranium.

Disease & pest resistance: Plants of the new Regal Geranium have not been observed to be resistant to pathogens and pests common to Regal Geraniums.

Temperature tolerance: Plants of the new Regal Geranium have been observed to tolerate temperatures ranging from about 1° C. to about 35° C. to 40° C.

It is claimed:

1. A new and distinct Regal Geranium plant named 'Regsal' as illustrated and described.

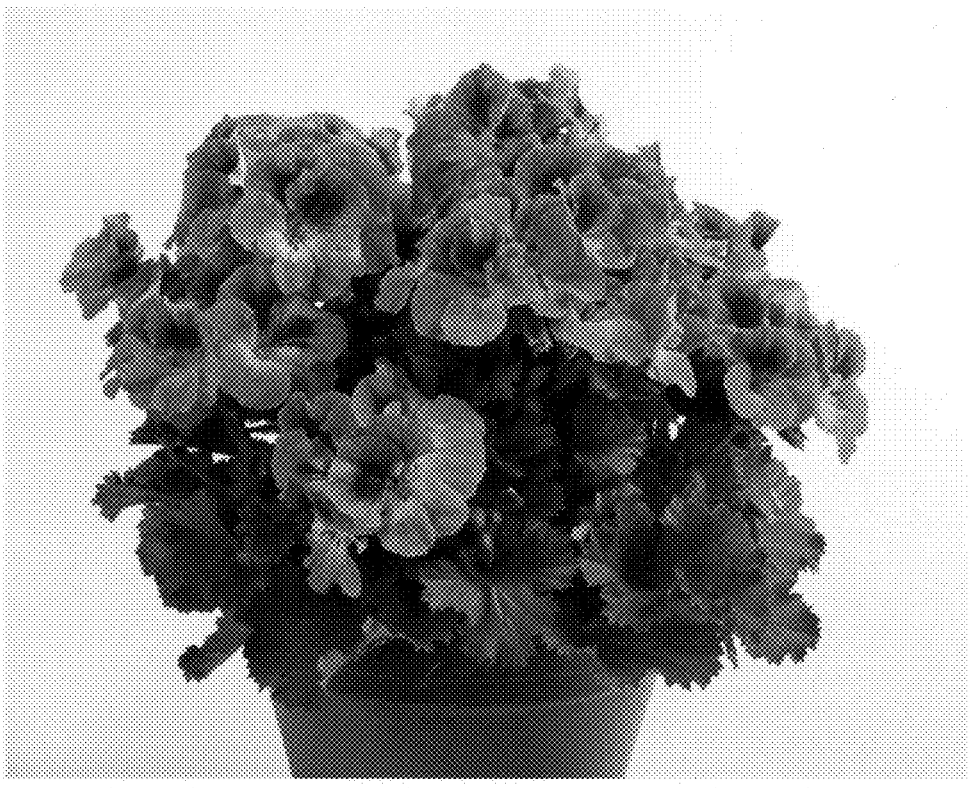

* * * * *